United States Patent [19]

Viegas et al.

[11] Patent Number: 5,071,644
[45] Date of Patent: Dec. 10, 1991

[54] TOPICAL DRUG DELIVERY WITH THERMO-IRREVERSIBLE GELS

[75] Inventors: Tacey X. Viegas; Lorraine E. Reeve, both of Ann Arbor; Raymond L. Henry, Grosse Pointe Woods, all of Mich.

[73] Assignee: Mediventures, Inc., Grosse Pointe Park, Mich.

[21] Appl. No.: 563,639

[22] Filed: Aug. 7, 1990

[51] Int. Cl.$^5$ .................. A61K 31/77; A61K 31/725; A61K 31/73

[52] U.S. Cl. ........................... 514/772.7; 424/486; 424/488; 523/122; 514/779; 514/944

[58] Field of Search ............... 424/78, 486, 427, 430, 424/436, 497; 514/944, 966, 967

[56] References Cited

U.S. PATENT DOCUMENTS

| | | | |
|---|---|---|---|
| 2,420,308 | 5/1947 | Gates | 252/316 |
| 2,426,125 | 8/1947 | Steiner | 260/209.6 |
| 3,535,307 | 10/1970 | Moss et al. | 260/209 |
| 3,640,741 | 2/1972 | Etes | 106/170 |
| 3,947,250 | 3/1976 | Pollack | 435/7 |
| 4,125,608 | 11/1978 | Blum et al. | 514/54 |
| 4,188,373 | 2/1980 | Krezanoski | 424/78 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,478,822 | 10/1984 | Haslam et al. | 424/78 |
| 4,676,976 | 6/1987 | Toba et al. | 424/485 |
| 4,795,642 | 1/1989 | Cohen et al. | 424/455 |
| 4,808,707 | 2/1989 | Daly et al. | 536/3 |
| 4,879,062 | 11/1989 | Moore | 514/789 |
| 4,917,886 | 4/1990 | Asche et al. | 424/81 |

OTHER PUBLICATIONS

In Vitro Evaluation of Alginate Gel Systems as Sustained Release Drug Delivery Systems, Stockwell, Jl. of Controlled Release, 3 (1986), pp. 167–175.

Release Characteristics of Herbicides from Ca Alginate Gel Formulations, Pfister et al., Jl. of Controlled Release, 3 (1986), pp. 229–233.

Primary Examiner—Thurman K. Page
Assistant Examiner—Edward J. Webman
Attorney, Agent, or Firm—Andrew E. Pierce

[57] ABSTRACT

Balanced pH, thermo-irreversible gels are ideal vehicles for drug delivery to the skin of a mammal.

43 Claims, 1 Drawing Sheet

RESISTANCE TO PENETRATION OF POLOXAMER-ALGINATE GEL vs. TEMPERATURE arrow denotes point of introduction of Calcium ions

TOPICAL DRUG DELIVERY WITH THERMO-IRREVERSIBLE GELS

BACKGROUND OF THE INVENTION

1. Field of the Invention

This invention relates to drug delivery systems comprising an aqueous gel.

2. Description of the Prior Art

Over the years, methods have been developed to achieve the efficient delivery of a therapeutic drug to a mammalian body part requiring pharmaceutical treatment. Use of an aqueous liquid which can be applied at room temperature as a liquid but which forms a semisolid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum below which a gel will not form.

In U.S. Pat. Nos. 4,474,751; '752; '753; and 4,478,822 drug delivery systems are described which utilize thermosetting gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; and 4,861,760. Thermosetting gel systems are also disclosed for application to injured mammalian tissues of the thoracic or peritoneal cavities in U.S. Pat. No. 4,911,926.

Ionic polysaccharides have been used in the application of drugs by controlled release. Such ionic polysaccharides as chitosan or sodium alginate are disclosed as useful in providing spherical agglomerates of water-insoluble drugs in the *Journal of Pharmaceutical Sciences* volume 78, number 11, November 1989, Bodmeier et al. Alginates have also been used as a depot substance in active immunization, as disclosed in the *Journal of Pathology and Bacteriology* volume 77, (1959), C. R. Amies. Calcium alginate gel formulations have also found use as a matrix material for the controlled release of herbicides, as disclosed in the *Journal of Controlled Release*, 3 (1986) pages 229 - 233, Pfister et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin, benzoquinone, etc.

In U.S. Pat. No. 4,795,642, there are disclosed gelatin-encapsulated, controlled-release compositions for release of pharmaceutical compositions, wherein the gelatin encloses a solid matrix formed by the cation-assisted gellation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or occular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Compositions and a process are disclosed for pharmaceutical compositions containing pharmacologically active medicaments useful in providing treatments to various parts of the mammalian body requiring pharmacological treatment. The pharmaceutical compositions in one embodiment of the invention provide a physiologically acceptable media having a buffered pH and an osmotically balanced vehicle so as to, preferably, provide an isotonic mixture which is iso-osmotic with body fluids and has a similar pH to body fluids, such as blood plasma and the extracellular fluid of exposed tissue, such as found in the area of third degree burn tissue. However, any desired pH and osmolality can be provided, for instance, the compositions of the invention can be formulated so as to be hyperosmotic to mammalian body tissues. The pH and osmotic pressure of such bodily fluids is about pH 7.4 and 290 mOsm/kg. In addition, the pharmaceutical compositions are, optionally, sterilized.

Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system.

The compositions of the invention in one embodiment comprise aqueous mixtures of a polyoxyalkylene polymer and an ionic polysaccharide, optionally containing a latent counter-ion to gel the polysaccharide upon release of the counter-ion and to render the gelled mixture irreversible upon cooling. The counter-ion can be microencapsulated in a heat sensitive medium, for instance, the walls of the microcapsule can be made of mono-, di-, or tri-glycerides or other natural or synthetic heat sensitive polymer medium. Alternatively, ion exchange resins can be incorporated in the compositions of the invention so as to release the desired counter-ion upon contact with an environment opposite in pH to the pH of the ion exchange resin. The aqueous mixture can be delivered to the area of the mammalian body requiring treatment as a low viscosity liquid at ambient temperatures which, upon contact with the mammalian body, forms a semi-solid gel having a very high viscosity. Alternatively, a two part system can be used in which the counter-ion instead of being present in a latent form, can be separately applied to the semi-solid gel formed by the polyoxyalkylene polymer upon contact with the mammalian body to further strengthen the gel. Because the preferred pharmaceutical compositions of the invention are low viscosity liquids at ambient temperatures, but form gels at mammalian body temperature, they easily pass around hair and reach the underlying skin insuring maximum contact between exposed tissue and the pharmaceutical composition of the invention. The pharmaceutical gel compositions of the invention can be either peeled away or allowed to be absorbed over time. The gels are gradually weakened upon exposure to mammalian body conditions.

A wide variety of polyoxyalkylene polymers are suitable for the preparation of the pharmaceutical compositions of the invention. Generally, it is necessary to adjust the polymer concentration in aqueous solution so as to obtain the desired sol-gel transition temperature in order that the compositions can be provided as low viscosity liquids at ambient temperature, yet form semi-solid gels at mammalian body temperatures. In addition to the concentration of the polymer and the concentration of the water soluble or dispersible pharmacologically active medicaments, other suitable excipients must be added so as to provide the desired isotonic and iso-osmotic properties.

The useful polymers which provide the sol-gel characteristics of the pharmaceutical compositions of the invention are, preferably, polyoxyalkylene block copolymers.

The ionic polysaccharides are natural polymers such as chitosan or alginates. Aqueous solutions of these ionic polysaccharides form gels upon contact with aqueous solutions of counter-ions such as calcium, strontium, aluminum, etc. or an aqueous solution of a tripolyphosphate.

DESCRIPTION OF THE DRAWING

The drawing provides a curve showing the penetration as measured by a Precision Universal Penetrometer of a 20mm thickness aqueous gel formed by combining Poloxamer 407 with sodium alginate and prepared in accordance with the procedure of Example 1. The scale at the left side of the plot indicates the depth of penetration, while the scale on the bottom of the plot indicates the temperature of the composition when tested. The arrow in the plot indicates the point at which an aqueous solution of calcium ions at a concentration of 0.137 Molar is made to contact the gelled poloxamer 407 solution so as to gel the polysaccharide component of the mixture.

DETAILED DESCRIPTION OF THE INVENTION

It has been found that aqueous pharmaceutical vehicles containing a polyoxyalkylene block copolymer, which have the unique feature, in a preferred embodiment, of being liquid at ambient temperatures and transitioning at mammalian body temperatures to a semi-solid gel, can be made resistant to shear thinning and the polyoxyalkylene gel made more resistant to penetration by the inclusion of a polysaccharide in admixture with the polyoxyalkylene and contacting the polysaccharide with a counter-ion to gel the polysaccharide The compositions can be made isotonic or iso-osmotic and adjusted to the pH of mammalian body fluids, such as blood plasma and extracellular fluid, as results in the area of third degree burns. The pH and osmotic pressure of such bodily fluids are 7.4 and 290 mOsm/kg, respectively. It is advantageous to deliver a pharmacologically active medicament to an area of the mammalian body requiring pharmacological treatment under pH and osmotic pressure conditions which match those of bodily fluids. It is also advantages to provide such compositions which are made more resistant to shear thinning as the result of higher gel strength. These advantages are obtained by the incorporation of an ionic polysaccharide in admixture with a polyoxyalkylene block copolymer. By matching the osmolality of the topical drug delivery compositions of the invention to those of bodily fluids, it is possible to eliminate burning or other discomfort upon topical application of the drug delivery composition of the invention. The higher gel strength compositions upon contact with a counter-ion for the ionic polysaccharide allow retention of the gel at the desired locus for longer intervals thus increasing the efficacy of action of the delivered drug. Optionally, the pharmaceutical compositions of the invention can be provided in a sterile condition.

The block copolymer compositions of the invention comprise: at least one polyoxyalkylene block copolymer of the formula $$Y[(A)_{\overline{n}}E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least about 60% by weight of the copolymer, n has a value such that the average molecular weight of A is at least about 500 to about 900, as determined by the hydroxyl number of a hydrophobe base intermediate, $$Y[(A)_{\overline{n}}H]_x \qquad (II)$$

and the total average molecular weight of the copolymer is at least about 5,000.

Generally, the polyoxybutylene-based block copolymers useful in the compositions of the invention are prepared by first condensing 1,2 butylene oxide with a water soluble organic compound initiator containing 1 to about 6 carbon atoms, such as, 1,4 butylene glycol or propylene glycol and at least 2 reactive hydrogen atoms to prepare a polyoxyalkylene polymer hydrophobe of at least about 500, preferably, at least about 1000, most preferably, at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

$$HO(C_2H_4O)_b(C_4H_8O)_a(C_2H_4O)_bH \quad (III)$$

wherein a and b are integers such that the hydrophobe base represented by ($C_4H_8O$) has a molecular weight of at least about 500, preferably, at least about 1000 and most preferably, at least about 3000, as determined by hydroxyl number, the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

$$HO(C_2H_4O)_b(C_3H_6O)_a(C_2H_4O)_bH \quad (IV)$$

wherein a and b are integers such that the hydrophobe base represented by ($C_3H_6O$) has a molecular weight of at least about 900, preferably, at least about 2500, most preferably, at least about 4000 average molecular weight, as determined by hydroxyl number; the polyoxyethylene chain constituting at least about 60%, preferably, at least about 70% by weight of the copolymer and the copolymer having a total average molecular weight of at least about 5000, preferably, at least about 10,000, and most preferably, at least about 15,000.

Polyoxyethylene-polyoxypropylene block copolymer adducts of ethylene diamine which can be used may be represented by the following formula:

wherein a and b are integers such that the copolymer may have (1) a hydrophobe base molecular weight of at least about 2000, preferably, at least about 3000, and most preferably, at least about 45u0, (2) a hydrophile content of at least about 60%, preferably, at least about 70% by weight, and (3) a total average molecular weight of at least about 5000, preferably, at least about 10,000, and most preferably, at least about 15,000.

The hydrophobe base of the copolymer of formula V is prepared by adding propylene oxide for reaction at the site of the four reactive hydrogen atoms on the amine groups of ethylene diamine. An ethylene oxide residue is used to cap the hydrophobe base. The hydrophile polyoxyethylene groups are controlled so as to constitute at least about 60%, preferably, at least about 70% by weight, and most preferably, at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C in water. When solution is complete the system is brought to room temperature whereupon it forms a gel. If the hot process of forming the gel is used the polymer is added to water heated to a temperature of about 75° C to about 85° C with slow stirring until a clear homogenous solution is obtained. Upon cooling, a clear gel is formed. Block copolymer gels containing polyoxybutylene hydrophobes must be prepared by the above hot process, since these will not liquify at low temperatures.

As used herein, the term gel is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylene diamine, and mixtures thereof and the like.

The oxypropylene chains can optionally contain small amounts of at least one of oxyethylene or oxybutylene groups. Oxyethylene chains can optionally contain small amounts of at least one of oxypropylene or oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5,000 to about 50,000, preferably, about 5,000 to about 35,000 and most preferably, about 10,000 to about 25,000. In addition to those polyoxyalkylene block copolymers described above, which are suitable in the formation of the pharmaceutical compositions of the invention, other polyoxyalkylene polymers which form gels at low concentrations in water are suitable. One such polymer is described in U.S. Pat. No. 4,810,503, incorporated herein by reference. These polymers are prepared by capping conventional polyether polyols with an alpha-olefin epoxide having an average of an about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant, which generally do not exceed 10% by weight total. Detailed methods of preparing these aqueous gels are disclosed in U.S. Pat. No. 4,810,503, incorporated herein by reference. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates.

These are then capped with the alpha-olefin epoxide to prepare the polymers. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C to 150° C, preferably from 80° C to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers. Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307; 3,036,118; 2,979,578; 2,677,700; and 2,675,619 incorporated herein by reference.

The surfactants may be ionic or non-ionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component than that dictated by economic considerations. However, the total amount of capped polymer and surfactant would generally not exceed 10 percent by weight.

In general, the preferred drug delivery system of the present invention will contain from about 0.01% to about 60% by weight of the medicament or pharmaceutical, from about 10 to about 50% by weight of the polyoxyalkylene polymer about 0.2 to about 2.5% by weight, preferably about 0.5 to about 1.5% by weight of alginate or chitosan ionic polysaccharides, and from 80% to about 20% by weight water. In special situations, however, the amounts may be varied to increase or decrease the dosage schedule. Generally, a molar ratio of counter-ion to chitosan or alginate of about 1:1 to about 10:1, preferably, about 2:1 to about 5:1, and, most preferably, about 3:1 to about 5:1 is used to render the compositions of the invention thermally irreversibly gelled.

If desired, the drug delivery vehicle may also contain preservatives, co-solvents, suspending agents, viscosity enhancing agents, osmolality adjusters, coloring agents, and other excipients in addition to the medicament and buffering agents. Suitable water soluble preservatives which may be employed in the drug delivery vehicle are sodium bisulfite, sodium thiosulfate, ascorbate, benzalkonium chloride, chlorabutanol, thimerosal, phenylmercuric borate, parabens, benzyl alcohol and phenyl ethanol, and others. These agents may be present in amounts of about 0.001% to about 5% by weight and, preferably, in the amount of about 0.01 to about 2% by weight.

Suitable water soluble buffering agents are alkali or alkali earth carbonates, phosphates, bicarbonates, citrates, borates, acetates, succinates and the like, such as sodium phosphate, citrate, borate, acetate, bicarbonate and carbonate. Organic buffering agents such as tromethamine (TRIS) may also be used. These agents are present in amounts sufficient to maintain the pH of the system at 7.4±0.2 and preferably 7.4. As such the buffering agent can be as much as 5% by weight of the total composition.

The ionic polysaccharides found useful in the present invention are hydrophilic colloidal materials and include the natural and synthetic proteins, natural and synthetic gums such as alginate gums, i.e., the alkali metal salts of alginic acid, pectin, and mixtures thereof as well as chitosan, which is a common name for the deacetylated form of chitin. Chitin is a natural product comprising poly-(N-acetyl-D-glucosamine). The alginates are available as dry powders from Protan Inc., Commack, New York or from Kelco Company, San Diego, California.

The alginates can be any of the water-soluble alginates including the ammonium and alkali metal (sodium, potassium, lithium, rubidium and cesium) salts of alginic acid and the soluble alginates of an organic base such as mono-, di-, or tri-ethanolamine, aniline and alike.

Useful divalent counter-ions for thermo-irreversibly gelling an alginate in combination with the polyoxyalkylene polymer compositions of the invention are cationic gelling agents, preferably, comprising an alkaline earth metal, most preferably, selected from the group consisting of calcium and strontium. Useful trivalent cations include aluminum The most preferred counter-ions for gelling an alginate aqueous solution are contained in ionic compounds selected from pharmaceutically-acceptable gluconates, flourides, citrates, phosphates, tartrates, sulfates, acetates, borates, chlorides, and the like having alkaline earth metal cations such as calcium and strontium. Especially preferred counter-ion containing inorganic salts for use as ionic polysaccharide gelling agents include such inorganic salts as the chloride salts, such as strontium chloride, calcium chloride, and mixtures thereof.

Generally, aqueous solutions of chitosan can be gelled with multivalent anion gelling agents. These preferably comprise water soluble metal or ammonium phosphates or polyphosphates such as an alkali metal or ammonium phosphates, polyphosphates, pyrophosphates, or metaphosphates. Useful counter-ions for gelling aqueous chitosan solutions are sodium and potassium tripolyphosphates, sodium and potassium pyrophosphates, sodium and potassium metaphosphates, and sodium and ammonium (mono-, di-, tri-) phosphates.

While the counter-ion, such as calcium or other counter-ions, may be obtained by contact with bodily fluids, it is preferred that the counter-ion in latent form be added to the ionic polysaccharide and polyoxyalkylene polymer compositions of the invention. Alternatively, the counter-ion can be added to the ionic polysaccharide and polyoxyalkalene polymer compositions of the invention utilizing a two part system in which the counter-ion is topically applied to the remaining components of the drug delivery system subsequent to their topical application to the skin. It is preferred to incorporate the counter-ion in a latent form together with the ionic polysaccharide and polyoxyalkylene polymer compositions of the invention. This may be accomplished by either encapsulating an aqueous solution of one of the counter-ion gelling agents, previously described above or by the incorporation of the counter-ion gelling agent into a matrix which provides for the controlled, slow-release of the gelling agent. For instance, the counter-ion can be incorporated into an ion exchange resin or gelatin-encapsulated controlled-release compositions can be used, as disclosed in U.S. Pat. No. 4,795,642, incorporated herein by reference. In this patent, there is disclosed the preparation of a gelatin shell encapsulating a controlled-release formulation in which the gelatin composition includes calcium chloride as a gelling agent. Alternatively, the counter-ion can be incorporated as an aqueous solution of a counter-ion gelling agent encapsulated in a vesicle composed, for instance, of alpha-tocopherol, as disclosed in U.S. Pat. No. 4,861,580, incorporated herein by reference. With specific reference to the use of the pharmaceutical compositions of the invention for administration to the skin of a mammal, it is contemplated to use suitable medicaments such as antibacterial substances, anti-infectives, anesthetics, anti-inflammatories, anti-parasitics, antivirals antifungals, analgesics, and diagnostics. Representative antibacterial substances are the antibacterial substance selected from the group consisting of beta-lactam antibiotics, tetracyclines, chloramphenicol, neomycin, gramicidin, bacitracin, sulfonamides, animoglysocide antibiotics, tobramycin, nitrofurazone, nalidixic acid and analogs, the antimicrobial combination of fludalanine/pentizidone, mafenide acetate, silver sulfadiazine, and nitrofurazone. Representative beta-lactam antibiotics or representative anti-infectives are iodine, chloramines, benzalkonium chloride and phenol. Representative anti-inflammatory drugs are cortisone, hydrocortisone, betamethasone, dexamethasone, fluocortolone, prednisolone, triamcinalone, indomethacine, sulindac and its salts and corresponding sulfide. A representative antiparasitic drug is ivermectin. Representative antiviral drugs are acyclovir and interferon. Representative anesthetic drugs are benzocaine, lidocaine and dibucaine. Representative antifungal drugs are tolnaftate, undecylenic acid, salicylic acid, zinc undecylenate miconazole, and thiabendazole. Representative analgesic drugs are methylsalicylate, menthol, camphor, methylnicotinate, triethanolamine salicylate, glycol salicylate and salicylamine. Representative diagnostic compounds are n-alkyl carbonates, cholesteryl oleyl carbonate, cholesteryl nonanoate or cholesteryl benzoate all in proper proportions to effect liquid crystal responses.

In general, the preferred drug delivery system of the present invention will contain from about 0.01% to about 60% by weight of the medicament or pharmaceutical, from about 10 to about 50% of the polymer and from 80% to about 20% water. In special situations, however, the amounts may be varied to increase or decrease the dosage schedule.

If desired, the drug delivery vehicle may also contain preservatives, co-solvents, suspending agents, viscosity enhancing agents, ionic strength and osmolality adjusters and other excipients in addition to the medicament and buffering agents. Suitable water soluble preservatives which may be employed in the drug delivery vehicle are sodium bisulfite, sodium thiosulfate, ascorbate, benzalkonium chloride, chlorabutanol, thimerosal, phenylmercuric borate, parabens, benzyl alcohol and phenyl ethanol and others. These agents may be present, generally, in amounts of about 0.001% to about 5% by weight and, preferably, in the amount of about 0.01 to about 2% by weight.

Suitable water soluble buffering agents are alkali or alkali earth carbonates, phosphates, bicarbonates, citrates, borates, acetates, succinates and the like, such as sodium phosphate, citrate, borate, acetate, bicarbonate carbonate and tromethamine (TRIS). These agents are present in amounts sufficient to maintain the pH of the system at 7.4±0.2 and, preferably, 7.4. As such the buffering agent can be as much as 5% on a weight basis of the total compostion.

Representative buffering agents or salts useful in maintaining the pH at about 7.4±0.2 are trimethamine and alkali or alkali earth carbonates, chlorides, sulfates, phosphates, bicarbonates, citrates, borates, acetates and succinates. Representative preservatives are sodium bisulfite, sodium thiosulfate, ascorbate, benzalkonium chloride, chlorobutanol, thimerosal, phenylmercuric borate, parabens, benzyl alcohol and phenyl ethanol.

The preparation of the pharmaceutical drug delivery compositions of the invention are described below. The Examples which follow were prepared according to the following preparation procedure. Since the polyoxyalkylenes dissolve more quickly and easily at reduced temperatures, the preferred methods of solubilization are to add the required amount of polymer to the amount of water to be used. Generally after wetting the polymer by shaking, the mixture is capped and placed in a cold chamber or in a thermostatic container at about 0° C. to 10° C. in order to dissolve the polymer. The mixture can be stirred or shaken to bring about a more rapid solution of the polymer. The pharmacologically active medicaments and various additives such as buffers, salts, and preservatives can subsequently be added and dissolved. In some instances the pharmacologically active substance must be suspended since it is insoluble in water. The pH of 7.4±0.2 is obtained by the addition of appropriate buffering agents. Other excipients maybe added to adjust osmolality or to provide other excipient attributes.

The following Examples illustrate the various aspects of the invention but are not intended to limit its scope. Where not otherwise specified throughout this specification and claims, temperatures are given in degrees centigrade and parts, percentages, and proportions are by weight.

EXAMPLE 1

Figure 1:
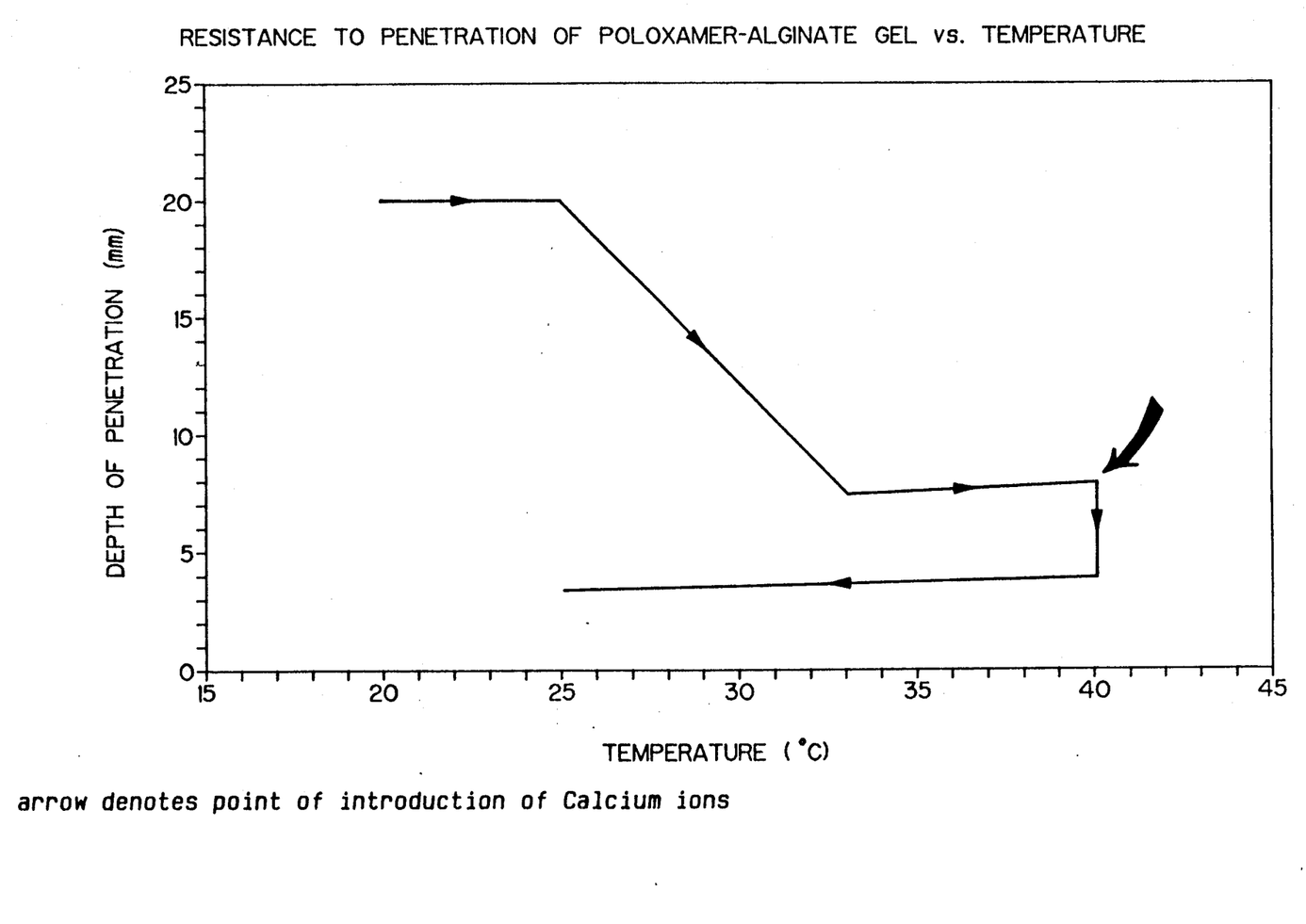

This Example formulation describes a composition characterized as iso-osmotic, sterile, and having a pH of 7.4±0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC® F-127 (also known as Poloxamer 407) by the BASF Corporation, Parsippany, N. J. A solution in TRIS hydrochloride buffer was made by dissolving said polymer and sodium alginate in cold (4° C.) buffer to give a concentration of 19% by weight polyoxyalkylene and 1% by weight sodium alginate. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

$$H[OCH_2CH_2]_{49}[OCHCH_2]_{67}[OCH_2CH_2]_{49}OH \quad\quad (VI)$$
with CH$_3$ branch This formulation forms the basis for the Figure in which the curve shows the penetration of a 20mm thickness aqueous gel at various temperatures. After contact of the gel with calcium ions, as indicated by the arrow at 40° C., the gel strength is not reduced or the composition rendered fluid by lowering the temperature back to 25° C.

EXAMPLE 2 (Inventive); EXAMPLE 3 (Control)

These examples describe hyperosmotic, pH balanced, thermo-sensitive systems, in which the active ingredient is dissolved. The following antibacterial formulations were prepared to contain 11.2 percent by weight mafenide acetate. The antibacterial formulations were prepared as follows:

| Ingredient | Percent by Weight | |
|---|---|---|
| | Example 2 | Example 3 |
| mafenide acetate | 11.2 | 11.2 |
| sodium alginate | 0.5 | — |
| carrageenan | — | 0.5 |
| Poloxamer 407 (BASF) | 19.0 | 19.0 |
| TRIS hydrochloride buffer (0.1 molar) | 69.3 | 69.3 |

The formulations were prepared by dissolving the drug and sodium alginate or carrageenan by stirring in the required amount of TRIS hydrochloride buffer. These ingredients were placed in a glass beaker in an ice bath and the Poloxamer 407 was added to the beaker slowly while stirring. After the Poloxamer 407 was completely dissolved, the formulation was stored at 4° C. The entire process was carried out under a nitrogen atmosphere. The product obtained was characterized as clear, straw colored and exhibiting gellation at the temperature of mammalian skin (33±2° C.). In the gelled state, the pH and osmolality of the preparation would be expected to be 7.5 and over 720 mOsm/Kg, respectively. Iso-osmotic solutions containing 2.5 to 3 % by weight would be expected to be iso-osmotic but less therapeutically effective. The solutions of Examples 2 and 3 were exposed to an equal amount of a 2% by weight solution of calcium chloride The solution of Example 2 formed a thermo-irreversible gel. The solution of Example 3 remained thermo-reversible.

Comparison of these examples illustrates the importance of utilizing an ionic polysaccharide (sodium alginate) instead of a non-ionic polysaccharide (carrageenan). In these examples, the 2% solution of calcium chloride was applied both as a spray to the solution of Examples 2 and 3 and also the 2% solution of calcium chloride was used to impregnate a gauze bandage and subsequently the solutions of Examples 2 and 3 were placed in contact with the gauze bandage. In both cases, the solution of Example 2 was rendered thermo-irreversible and the solution of Example 3 was unaffected.

EXAMPLES 4 and 5

Examples 2 and 3 are repeated substituting for Poloxamer 407, 2% by weight of polymer #2, as described in U.S. Pat. NO. 4,810,503 and 4% by weight of surfactant #1, as described therein. The balance of the percentage of Poloxamer 407 used in Examples 2 and 3 is made up with TRIS hydrochloride buffer. These formulations form soft gels at room temperature which are usefully stiffened upon exposure to a 2% by weight aqueous solution of calcium chloride, in the case of Example 4 and are unaffected in the case of control Example 5. Substantially similar pH and osmolality results are obtained.

EXAMPLE 6

Ion exchange resin beads sold under the tradename Duolite were treated so as to incorporate calcium by first treating a 30 gram sample of the ion exchange resin with a solution of 0.1 molar hydrochloric acid so as to allow for the exchange of protons for sodium. After three washings with 0.1 molar hydrochloric acid, the beads were washed with water and then washed twice with a 2% aqueous solution of calcium chloride Each of the washing steps took place over a period of 16 hours (overnight). The beads were thereafter filtered and washed with water utilizing coarse filter paper and a Buchner glass filter assembly The beads were then left overnight in a desiccator to dry. The dried beads of ion exchange resin which were obtained were utilized in the amount of 2 grams to fill a first compartment (close to the needle of the syringe) of a glass syringe utilized to apply liquids and dry materials. The syringe is sold under the tradename Hypak. Into the second compartment of the syringe, there was placed the solution of Example 2. Pushing the plunger of the syringe forward resulted in mixing the solution of Example 2 with the ion exchange beads. After 5 to 10 minutes subsequent to mixing, the mixture was expelled from the syringe. After an additional 15 minutes the expelled material formed a thermo-irreversible film on the substrate on which it was expelled.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. A hyperosmotic, isoosmotic, or hypoosmotic aqueous pharmaceutical composition having a osmolality and buffered pH, which is a liquid at room temperature or below and a thermo-reversible gel at mammalian body temperature, for administration to the skin of a mammal, said gel consisting essentially of water, an ionic polysaccharide, A) a polyoxyalkylene block copolymer of the formula $$Y[(A)_{\overline{n}}E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least 60% by weight of the copolymer, n has a value such that the average molecular weight is at least about 500 to about 900, as determined by the hydroxyl number of an intermediate, $$Y[(A)_{\overline{n}}H]_x \qquad (II)$$

and the total average molecular weight of the copolymer is at least about 5000,

B) a pharmacologically effective amount of a drug selected from the group consisting of antibacterials, antiinflammatories, antiparasitics, antivirals, anesthetics, antifungals, analgesics, and diagnostics, and C) a pharmaceutically acceptable buffer sufficient to maintain the pH of said aqueous composition at a desired level, and, optionally, a latent form of a counter-ion capable of thermo-irreversibly gelling the ionic polysaccharide.

2. The composition of claim 1, wherein said copolymer is prepared using a water soluble organic compound initiator (Y) having 1 to about 6 carbon atoms and wherein the pH is maintained at 7.4±0.2.

3. The composition of claim 2, wherein said polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol, trimethylolpropane, ethylenediamine and mixtures thereof.

4. The composition of claim 3, wherein said copolymer is a polyoxyethylene-polyoxypropylene block copolymer wherein said polyoxyethylene moiety constitutes at least about 70% by weight of the copolymer, the average molecular weight of A is at least about 1200, and the total molecular weight of the copolymer is at least about 10,000.

5. The composition of claim 4, wherein the intermediate of Formula II is prepared by initiation with propylene glycol and has a molecular weight of at least about 1500.

6. The composition of claim 5, wherein said copolymer has the formula:

$$HO(C_2H_4O)_b(C_4H_8O)_a(C_2H_3O)_bH \qquad (III)$$

wherein in III, a and b are integers such that the hydrophobe base represented by $(C_4H_8O)_a$ has a molecular weight of at least about 500 as determined by hydroxyl number, the polyoxyethylene chain constituting at least about 70% by weight of the copolymer, and the copolymer having a total average molecular weight of at least 15,000, or $$HO(C_2H_4O)_b(C_3H_6O)_a(C_2H_4O))_bH \qquad (IV)$$

wherein in IV, a and b are integers such that the hydrophobe base represented by $(C_3H_6O)_a$ has a molecular weight of at least about 900 average molecular weight, as determined by hydroxyl number, the polyoxyethylene chain constitutes at least about 70% by weight of the copolymer, and the copolymer having a total average molecular weight of at least about 15,000, or wherein in V, a and b are integers such that the copolymer has a hydrophobe molecular weight of at least about 1500, a hydrophile content of at least about 70%, and a total average molecular weight of at least about 15,000.

7. The composition of claim 6, wherein said polyoxyalkylene block copolymer is $$H[OCH_2CH_2]_{49}[OCHCH_2]_{67}[OCH_2CH_2]_{49}OH \qquad (VI)$$
$$\qquad\qquad\qquad |$$
$$\qquad\qquad\quad CH_3$$

present in the amount of about 10 to about 40% by weight of the total weight of said composition.

8. The composition of claim 7, wherein said polyoxyalkylene block copolymer is present in the amount of about 15 to about 30% by weight of said aqueous composition, said counter-ion is present as a microencapsulated component or incorporated with an ion exchange resin and is selected from the group consisting of at least one of calcium, strontium, and aluminum and said ionic polysaccharide is selected from the group consisting of an ammonium alginate, an alkali metal alginate, and mixtures thereof.

9. The composition of claim 7, wherein said polyoxyalkylene block copolymer is present in the amount of about 15 to about 30% by weight of said aqueous composition, the optional latent form of said counter-ion is present as a microencapsulated component or incorporated with an ion exchange resin and is selected from the group consisting of at least one of the metal phosphates, metaphosphates, pyrophosphates, and tripolyphosphates, and said ionic polysaccharide is chitosan.

10. A process for treating a condition requiring the application of a medicament, which comprises administering to the skin of a mammal a hyperosmotic, isoosmotic, or hypoosmotic buffered pH, which is at room temperature or below and a thermo-reversible gel at mammalian body temperature, said gel consisting essentially of water, an ionic polysaccharide, A) a polyoxyalkylene block copolymer of the formula $$Y[(A)_{\overline{n}}E-H]_x \quad (I)$$

wherein A is a polyoxyalkylene moiety having an oxygen/carbon atom ratio of less than 0.5, x is at least 1, Y is derived from water or an organic compound containing x reactive hydrogen atoms, E is a polyoxyethylene moiety, n has a value such that the average molecular weight of A is at least about 500 to about 900, as determined by the hydroxyl number of an intermediate, $$Y[(A)_{\overline{n}}H]_x \quad (II)$$

and wherein the total average molecular weight of the copolymer is at least about 5000, B) a pharmacologically effective amount of a drug selected from the group consisting of antibacterials, antiinflamatories, antiparasitics, antivirals, anesthetics, antifungals, analgesics, and diagnostics, and C) a pharmaceutically acceptable buffer sufficient to maintain the pH of said aqueous composition at a desired level and, optionally, a latent form of a counter-ion capable of thermo-irreversibly gelling the ionic polysaccharide.

11. The process of claim 10, wherein Y in said formulas I and II is a water soluble organic compound having 1-6 carbon atoms, and said copolymer is selected from the group consisting of a polyoxyethylene-polyoxybutylene block copolymer, a polyoxyethylene-polyoxypropylene block copolymer and mixtures thereof, and wherein the polyoxyethylene moiety constitutes at least 70% by weight of the polymer, and wherein the pH is maintained at about 7.4±0.2.

12. The process of claim 11, wherein said copolymer is selected from block copolymers which form aqueous gels at a concentration of about 10-50% by weight of the total weight of said composition.

13. The process of claim 12, wherein said Y is a compound selected from the group consisting of propylene glycol, glycerin, pentaerythritol, trimethylolpropane, ethylenediamine, and mixtures thereof.

14. The process of claim 13, wherein Y is derived from propylene glycol, A is the residue of propylene oxide, and the intermediate of Formula II has an average molecular weight of at least about 900.

15. The process of claim 14, wherein Y is derived from butylene glycol, A is the residue of butylene oxide, and the intermediate of Formula II has an average molecular weight of at least about 500.

16. The process of claim 15, wherein said copolymer has the formula $$HO(C_2H_4O)_b(C_4H_8O)_a(C_2H_4O)_bH \quad (III)$$

wherein in III, a and b are integers such that the hydrophobe base represented by (C4H8O) has a molecular weight of at least 1000, as determined by hydroxyl number, the polyoxyethylene chain constitutes at least about 60% by weight of the copolymer, and the copolymer has a total average molecular weight of at least 5,000, 10 or $$HO(C_2H_4O)_b(C_3H_6O)_a(C_2H_4O)_bH \quad (IV)$$

wherein in IV, a and b are integers such that the hydrophobe base represented by (C3H6O) has a molecular weight of at least about 1500 average molecular weight, as determined by hydroxyl number, the polyoxyethylene chain constitutes at least about 60% by weight of the copolymer, and the copolymer has a total average molecular weight of at least 5,000, or (V)

wherein V, a and b are integers such that the copolymer has a hydrophobe molecular weight of at least 2000, a hydrophile content of at least about 60%, and a total average molecular weight of at least about 5,000.

17. The process of claim 16, wherein said copolymer is $$H(OCH_2CH_2)_{49}[OCHCH_2]_{67}(OCH_2CH_2)_{49}OH. \quad (VI)$$
$$\overset{|}{CH_3}$$

18. The process of claim 17, wherein said counter-ion is derived from a compound selected from the group consisting of at least one of the metal phosphates, metaphosphates, pyrophosphates and tripolyphosphates and said ionic polysaccharide is chitosan, and said counter-ion is present as a microencapsulated component or incorporated with an ion exchange resin.

19. The process of claim 17 wherein said counter-ion is selected from the group consisting of at least one of calcium, strontium, and aluminum, said ionic polysaccharide is selected from the group consisting of an ammonium alginate, an alkali metal alginate, and mixtures thereof, and said counter-ion is present as a microencapsulated component or incorporated with an ion exchange resin.

20. A process for treating a condition requiring the application of a medicament which comprises administering to the skin of a mammal a hyperosmotic, isoosmotic, or hypoosmotic composition, having a buffered pH, consisting essentially of water, an ionic polysaccharide, a surfactant, a polyoxyalkylene polyether having a molecular weight of about 10,000 to about 100,000 which is selected from the group consisting of A) polyoxyalkylene polyethers prepared by reacting ethylene oxide and at least one lower alkylene oxide having 3 to 4 carbon atoms with at least one active hydrogen containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether, B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether, C) a pharmacologically effective amount of a drug selected from the group consisting of antibacterials, antiinflammatories, antiparasitics, antivirals, anesthetics, antifungals, analgesics, and diagnostics, and D) a pharmaceutically acceptable buffer sufficient to maintain the pH of said aqueous composition at a desired level, and, optionally, a latent form of a counter-ion capable of thermo-irreversibly gelling the ionic polysaccharide.

21. The process of claim 20, wherein said polyether is prepared using a heteric copolymer intermediate and wherein the pH is maintained at about 7.4±0.2.

22. The process of claim 21, wherein said polyether is prepared using an alpha-olefin oxide having an average carbon chain length of about 20 to 30 carbon atoms, present in the amount of about 0.3 to 10 percent of the total weight of said polyether.

23. The process of claim 22, wherein said polyether contains a proportion of ethylene oxide residue to the residue of said lower alkylene oxide of about 70 to about 90 percent by weight of ethylene oxide residue to about 30 to about 10 percent by weight of said lower alkylene oxide residue.

24. The process of claim 23, wherein said polyether is prepared using propylene oxide as the lower alkylene oxide.

25. The process of claim 20, wherein said polyether is prepared using a block copolymer intermediate.

26. The process of claim 25, wherein said polyether is prepared using an alpha-olefin oxide having an average carbon chain length of about 20 to 30 carbon atoms, present in the amount of about 0.3 to 10 percent of the total weight of said polyether.

27. The process of claim 26, wherein said polyether is prepared using a proportion of ethylene oxide residue to the residue of said lower alkylene oxide of from about 70 to about 90 percent by weight of ethylene oxide residue to about 30 to about 10 percent by weight of said lower alkylene oxide residue.

28. The process of claim 27, wherein said polyether is prepared using propylene oxide as the alkylene oxide said 29. The process of claim 20, wherein polyether is polyether (B) of claim 19.

30. The process of claim 29, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of at least one of the metal phosphates, metaphosphates, pyrophosphates, and tripolyphosphates, said ionic polysaccharide is chitosan, and said counter-ion is present as a microencapsulated component or incorporated with an ion exchange resin.

31. The process of claim 29, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of at least one of calcium, strontium, and aluminum, said ionic polysaccharide is selected from the group consisting of an ammonium alginate, an alkali metal alginate, and mixtures thereof, and said counter-ion is present as a microencapsulated component or incorporated with an ion exchange resin.

32. A hyperosmotic, isoosmotic, or hypoosmotic aqueous pharmaceutical composition having a buffered pH for administration to the skin of a mammal to treat a condition requiring the application of a medicament, said composition consisting essentially of water, an ionic polysaccharide, a surfactant, a polyether having a molecular weight of about 10,000 to about 100,000 which is selected from the group consisting of A) polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether and B) polyethers prepared by reacting ethylene oxide with at least one active hydrogen containing compound having from 2 to 10 carbon atoms and from 2 to 6 active hydrogens to prepare a homopolymer intermediate and further reacting said homopolymer with at least one alpha-olefin oxide having an average carbon chain length of about 20 to 45 aliphatic carbon atoms; and wherein said alpha-olefin oxide is present in the amount of about 0.3 to 10 percent by weight based on the total weight of said polyether, C) a pharmacologically effective amount of a drug selected from the group consisting of antibacterials, antiinflammatories, antiparasitics, antivirals, anesthetics, antifungals, analgesics, and diagnostics, and D) a pharmaceutically acceptable buffer sufficient to maintain the pH of said aqueous composition at a desired level, and, optionally, a latent form of a counter-ion capable of thermo-irreversibly gelling the ionic polysaccharide.

33. The composition of claim 32, wherein said polyether is prepared using a heteric copolymer intermediate and wherein the pH is maintained at 7.4 ±0.2.

34. The composition of claim 33, wherein said polyether is prepared using an alpha-olefin oxide having an average carbon chain length of about 20 to 30 carbon atoms, present in the amount of about 0.3 to 10 percent of the total weight of said polyether.

35. The composition of claim 34, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

36. The composition of claim 35, wherein said polyether is prepared using propylene oxide as the lower alkylene oxide.

37. The composition of claim 32, wherein said polyether is prepared using a block copolymer intermediate.

38. The composition of claim 37, wherein said polyether is prepared using an alpha-olefin oxide having an average carbon chain length of about 20 to 30 carbon atoms, present in the amount of about 0.3 to 10 percent of the total weight of said polyether.

39. The composition of claim 38, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

40. The composition of claim 39, wherein said polyether is prepared using propylene oxide as the lower alkylene oxide.

41. The composition of claim 32, wherein said polyether is polyether (B) of claim 32.

42. The composition of claim 41, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of at least one of calcium, strontium, and aluminum, said ionic polysaccharide is selected from the group consisting of an ammonium alginate, an alkali metal alginate, and mixtures thereof and said counter-ion is present as a microencapsulated component or incorporated with an ion exchange resin.

43. The composition of claim 41, wherein said polyether is prepared using an alpha-olefin oxide having an average carbon chain length of about 20 to 30 carbon atoms, present in the amount of about 0.3 to 10 percent of the total weight of said polyether, said counter-ion is selected from the group consisting of at least one of the metal phosphates, metaphosphates, pyrophosphates, and tripolyphosphates, said ionic polysaccharide is chitosan and said counter-ion is present as a microencapsulated component or incorporated with an ion exchange resin.

* * * * *

UNITED STATES PATENT AND TRADEMARK OFFICE
CERTIFICATE OF CORRECTION

PATENT NO. : 5,071,644

DATED : December 10, 1991

INVENTOR(S) : Tacey X. Viegas, Lorraine E. Reeve, et al

It is certified that error appears in the above-identified patent and that said Letters Patent is hereby corrected as shown below:

Column 5, Line 50, "45u0" should read ---4500---.

Column 13, Lines 11 and 12, delete "osmolality and".

Column 16, Line 1, after "5000", delete ---10---.

Column 16, Line 7, "C3H6O" should read ---$C_3H_6O$---.

Signed and Sealed this

First Day of June, 1993

Attest:

MICHAEL K. KIRK

Attesting Officer

Acting Commissioner of Patents and Trademarks